United States Patent [19]
Wiedenfeld

[11] Patent Number: 5,624,261
[45] Date of Patent: Apr. 29, 1997

[54] COMPOSITE RESIN VENEER

[76] Inventor: Kenneth R. Wiedenfeld, 13818 Seahorse Ave., Corpus Christi, Tex. 78418

[21] Appl. No.: 512,928

[22] Filed: Aug. 9, 1995

[51] Int. Cl.$^6$ .............................. A61C 5/08; A61C 5/10
[52] U.S. Cl. ..................... 433/222.1; 433/223; 433/218
[58] Field of Search .......................... 433/218, 222.1, 433/223, 212.1, 216

[56] References Cited

U.S. PATENT DOCUMENTS

| | | | |
|---|---|---|---|
| 5,275,561 | 1/1994 | Goldsmith | 433/216 |
| 5,284,442 | 2/1994 | Peterson | 433/223 |
| 5,314,335 | 5/1994 | Fung | 433/223 |
| 5,332,390 | 7/1994 | Rosellini | 433/34 |
| 5,342,201 | 8/1994 | Oden | 433/223 |
| 5,346,397 | 9/1994 | Braiman | 433/223 |
| 5,378,154 | 1/1995 | Van Der Zel | 433/223 |
| 5,487,663 | 1/1996 | Wilson | 433/223 |

*Primary Examiner*—Cary E. O'Connor
*Attorney, Agent, or Firm*—Gregory J. Gore

[57] ABSTRACT

A veneer for primary teeth in children, composed of composite resin, provides an aesthetically pleasing restoration which displays good fit, durability, and is inexpensive. A composite resin veneer is adhered to a properly fitted stainless steel crown which has been sandblasted and primed. The veneer of the present invention is then selected from a kit of different sized veneers which corresponds to the crown size that has been used. A composite resin cement is used to cement the facing to the fitted stainless steel crown. The veneer crown is then cemented to the patient's tooth.

4 Claims, 1 Drawing Sheet

5,624,261

COMPOSITE RESIN VENEER

FIELD OF THE INVENTION

This invention relates to dental facings or veneers for human teeth. More specifically, it relates to veneers applied to stainless steel crowns.

BACKGROUND OF THE INVENTION AND DESCRIPTION OF PRIOR ART

Primary anterior teeth that require extensive restorative therapy due to caries, trauma, or developmental defects can present a particularly challenging problem to the dentist. The ideal restorative technique would assure strength, durability, aesthetics, and efficiency in placement. Many of the currently available regimens fail to fulfill one or more of the goals mentioned above; couple these concerns with the technical difficulties of operating on children with behavior management problems, and the dentist is often left with few reliable restorative options.

Restorative modalities currently in use to treat primary anterior teeth include bonding with composite resin, as in strip crowns, polycarbonate crowns, conventional stainless steel crowns, open-faced stainless steel crowns, and commercially veneered stainless steel crowns. However, each of these techniques presents technical, functional, or aesthetic compromises that complicate their efficient and effective use.

Bonding with composite resin requires an environment free of salivary or blood contaminants. Even though the results in a cooperative patient can be aesthetically pleasing, heavy functional loads, coupled with inadequate retention, often result in unpredictable longevity. Polycarbonate crowns are associated with the common clinical problems of fracture, debonding, and dislodgement. Conventional stainless steel crowns have excellent longevity and ease of placement when compared to bonding; they often result, however, in poor aesthetics. Open-faced stainless steel crowns result in some metal being exposed, which is an aesthetic concern. In addition, facings may become dislodged and the patient time required for fabrication is significantly greater than that of conventional stainless steel crowns. Finally, commercially veneered stainless steel crowns are often difficult to fit, due to problems with trimming and crimping of the preveneered surfaces.

The most relevant patent prior art of which the applicant is aware is U.S. Pat. No. 5,332,390, entitled "Shell Tooth Form", issued to Rosellini on Jul. 26, 1994. This patent describes the method for providing a crown or a replacement tooth utilizing the in situ production of preparing the tooth by grinding and shaping; filling a transparent shell tooth form with light-setting resin; placing the shell form onto the prepared tooth; and bonding the resin between the form and the tooth. While this reference discloses the use of a transparent shell formed from a light-setting resin, it does not indicate application to stainless steel crowns, or that a partial covering surface formed of a light-setting resin, such as a veneer, may be employed.

There is therefore a need in the dental arts for an easy and convenient, chairside technique that provides dental restoration with the strength and adaptability of a plain stainless steel crown, while at the same time providing the aesthetics of a plastic crown.

BRIEF SUMMARY OF THE INVENTION

In order to meet the need in the dental arts described above, the present invention utilizes advances in restorative materials in metal-bonding procedures that combines the advantages of stainless steel crowns with cosmetics of composite restorative materials. This results in an efficient, chairside, restorative technique of the present invention that can be used economically to treat primary anterior teeth with durable and aesthetically pleasing results. The present invention includes a set of pre-formed composite resin veneers. These facings are pre-made to fit the fronts, tops, and sides of various sizes of commercially available stainless steel crowns. The present invention utilizes materials which are already used and approved for dentistry, with the exception of the prefabricated composite resin facings as further described herein.

Dentists are presently using a similar technique to attach porcelain facings to the front, top and side surfaces of permanent front teeth in adults. However, this alternative is not suitable for primary teeth in children, because the porcelain veneers are extremely expensive and must be custom-manufactured by a laboratory. As a result, the procedure becomes expensive due to repeated visits to the dental office for a treatment that will be short due to the limited life of the primary tooth.

It is therefore the main object of the present invention to create a pre-formed, composite resin veneer for stainless steel crowns which may be easily applied chairside in one visit. It is a further object of the present invention to provide an aesthetically pleasing restoration for primary anterior teeth which displays a good fit, good durability, and which is inexpensive. Other objects and advantages of the present composite resin veneer and restorative dental method will become more apparent to those of ordinary skill in the art from the following drawings and detailed description of the preferred embodiment.

DESCRIPTION OF THE PREFERRED EMBODIMENT

Figure 1:
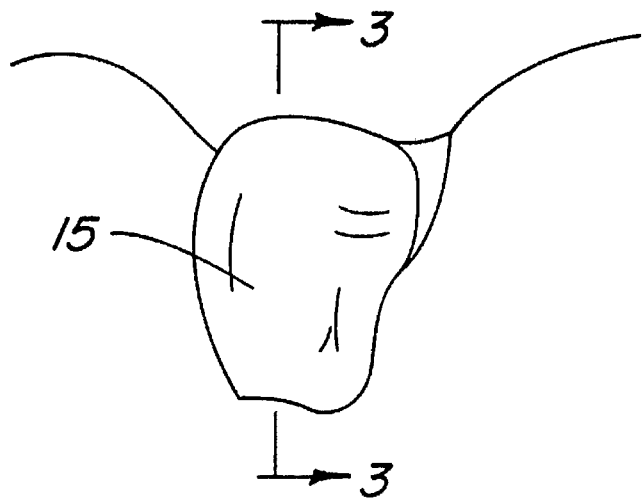
FIG. 1 is a right front isometric view of the present invention.
Figure 2:
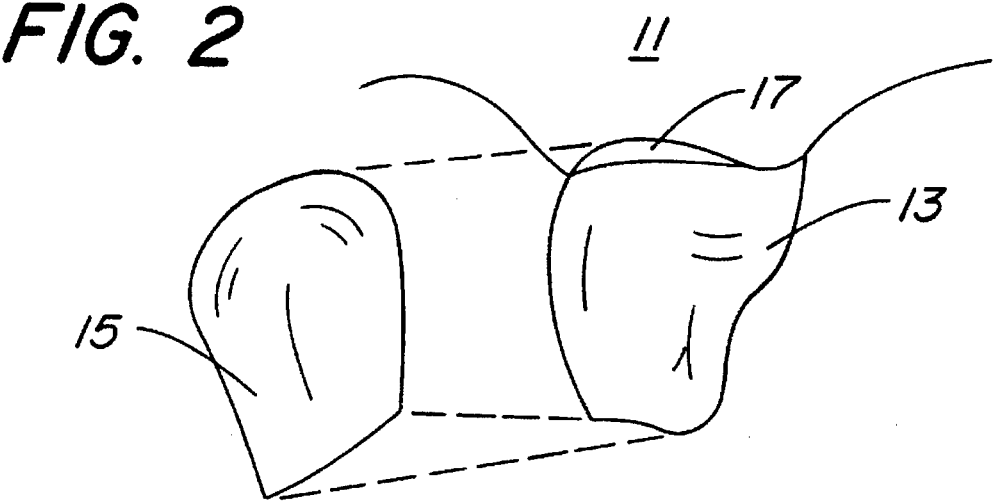
FIG. 2 is a right front isometric assembly view showing the composite resin facing of the present invention applied to a stainless steel crown.
Figure 3:
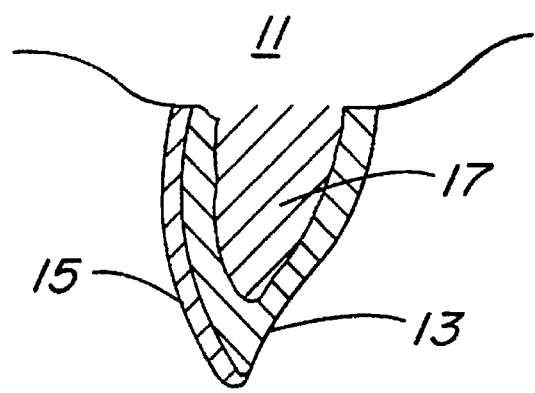
FIG. 3 is a side-sectional view of the present invention applied over the front face of a steel crown.

FIG. 1 shows composite resin veneer 15 applied to the front of a crowned tooth. Referring now to FIG. 2, tooth 17 is shown with metal crown 13 applied, which is preferably composed of stainless steel. In this drawing, a slight margin is shown between crown 13 and gingiva 11. The pre-formed composite resin facing 15 is cup-shaped to fit over the front, top and sides of stainless steel crown 13. Referring now to FIG. 2, a side-sectional view of the tooth shown in FIG. 1 with the facing applied is shown. As will be explained further herein, the facing is secured to the stainless steel crown with a composite resin cement. Stainless steel crown 13 which has been fitted over tooth 17 and has been long used in dentistry for their durability and good fit.

The method and technique of the present invention are as follows. Anterior teeth that could benefit from restoration with stainless steel crowns are selected for treatment. These teeth are prepared in a manner that allows the operator to select slightly under-contoured stainless steel crowns. This step allows for a more naturally contoured veneered crown, because the addition of the composite facing adds to the crown's overall dimensions. The selection of the crowns, trimming and crimping are completed as necessary.

Thereafter, the following technique is used to veneer the crowns at chairside:

(1) The dentist prepares primary anterior teeth for stainless steel crowns.
(2) The fabricated stainless steel crowns are adapted and completely fitted.
(3) The stainless steel crown is then removed from the tooth and the front side and top are sandblasted and then air-dried to remove excess aluminum oxide.
(4) Two coats of metal primer are then applied to the sandblasted areas.
(5) The pre-formed composite resin veneer of the present invention corresponding to the crown size is etched with an acid-etching agent and then washed with water and air dried.
(6) A composite resin cement is then used to cement the facing to the fitted stainless steel crown. The dentist then takes it back to the mouth for a fitting and an adjustment, if needed, prior to final cementation to the tooth.

The objects of the present invention have therefore been achieved because the pre-formed facing of the present invention and the new chairside technique provide the strength and adaptability of a stainless steel crown, while providing an aesthetically pleasing crown, that can be performed quickly, easily and inexpensively. This makes the crown facing and technique of the present invention particularly well-suited to restoration of primary anterior teeth.

It should be understood that the above description discloses specific embodiments of the present invention and are for purposes of illustration only. There may be other modifications and changes obvious to those of ordinary skill in the art that fall within the scope of the present invention which should be limited only by the following claims and their legal equivalents.

What is claimed is:

1. A kit for restorative dentistry, comprising:
   a plurality of metal crowns for fitting over teeth;
   a plurality of pre-formed composite resin veneers for affixing to crowned teeth in situ; and
   a composite resin cement for affixing said pre-formed composite resin veneers to said metal crowns.
2. The dental restorative kit of claim 1, wherein said metal crowns are composed of stainless steel.
3. The dental restorative kit of claim 2, wherein said composite resin veneers are cup-shaped and cover a front, top and sides of said stainless steel crowns.
4. The method for restoring a damaged human tooth, comprising:
   pre-fitting a stainless steel crown about said damaged tooth;
   removing said stainless steel crown and sandblasting a from, sides and a top of said crown;
   air-drying said crown to remove excess aluminum oxide;
   applying metal primer to the sandblasted areas;
   selecting one facing from a plurality of pre-formed composite resin facings;
   preparing said one facing by applying an acid-etching agent, washing with water, and then air-drying;
   cementing said prepared composite resin facing to the fitted stainless steel crown using a composite resin cement; and
   cementing said crown with said applied facing to said damaged tooth.

* * * * *